United States Patent
Ingram et al.

(10) Patent No.: US 10,898,414 B2
(45) Date of Patent: Jan. 26, 2021

(54) SYSTEM AND METHOD FOR METERED ENTERAL FEEDING

(71) Applicant: NEOMED, INC., Woodstock, GA (US)

(72) Inventors: Aaron N. Ingram, Canton, GA (US); Anthony C. Lair, Alpharetta, GA (US); Mark Martin Costello, County Mayo (IE); Tony Doherty, County Mayo (IE); Benjamin Martin Davis, Woodstock, GA (US)

(73) Assignee: NeoMed, Inc., Woodstock, GA (US)

( * ) Notice: Subject to any disclaimer, the term of this patent is extended or adjusted under 35 U.S.C. 154(b) by 1412 days.

(21) Appl. No.: 13/959,394

(22) Filed: Aug. 5, 2013

(65) Prior Publication Data
US 2014/0039462 A1 Feb. 6, 2014

Related U.S. Application Data (60) Provisional application No. 61/680,124, filed on Aug. 6, 2012.

(51) Int. Cl.
*A61J 15/00* (2006.01)
*A61M 5/14* (2006.01)
(Continued)

(52) U.S. Cl.
CPC ....... *A61J 15/0096* (2013.01); *A61J 15/0092* (2013.01); *A61M 5/1414* (2013.01); *A61M 39/26* (2013.01); *A61M 2005/3123* (2013.01)

(58) Field of Classification Search
CPC .... A61J 15/00; A61J 15/0026; A61J 15/0096; A61J 15/0092; A61M 39/285; A61M 39/286; A61M 2005/3123
See application file for complete search history.

(56) References Cited

U.S. PATENT DOCUMENTS 3,113,873 A 12/1963 Krause
3,731,684 A 5/1973 Spiegel
(Continued)

FOREIGN PATENT DOCUMENTS

DE 2108381 B2 8/1972
DE 29617949 U1 4/1997
(Continued)

OTHER PUBLICATIONS

International Search Report & Written Opinion for PCT/US12/60987; dated Jan. 25, 2013; 13 pgs.
(Continued)

*Primary Examiner* — Nathan R Price
*Assistant Examiner* — Weng Lee
(74) *Attorney, Agent, or Firm* — Dority & Manning, P.A.

(57) ABSTRACT

A metered enteral feeding system for delivering fluids, the metered enteral feeding system including a vented container with contained volume for containing the fluids. The metered enteral feeding system includes a discharge port for discharging the fluid from the contained volume and at least one vent for allowing airflow into the contained volume. The metered enteral feeding system also includes a flow control valve in fluid communication with the discharge port of the vented container. The fluid control valve is adjustable to provide an increased or decreased flowrate therethrough.

15 Claims, 11 Drawing Sheets

(51) Int. Cl.
*A61M 5/31* (2006.01)
*A61M 39/26* (2006.01)

(56) References Cited

U.S. PATENT DOCUMENTS

| | | | |
|---|---|---|---|
| 3,885,562 A | 5/1975 | Lampkin | |
| 3,900,184 A * | 8/1975 | Burke | A61M 39/286 |
| | | | 251/6 |
| 4,356,824 A | 11/1982 | Vazquez | |
| 4,392,851 A | 7/1983 | Elias | |
| D282,962 S | 3/1986 | Gerber | |
| D307,795 S | 5/1990 | Frantz | |
| 4,994,048 A | 2/1991 | Metzger | |
| 5,137,527 A | 8/1992 | Miller et al. | |
| 5,279,566 A | 1/1994 | Kline, Jr. et al. | |
| 5,460,603 A | 10/1995 | DeSantis | |
| 5,549,550 A | 8/1996 | Mazer et al. | |
| 5,611,787 A | 3/1997 | Demeter et al. | |
| 5,746,715 A | 5/1998 | Mazer et al. | |
| 5,755,689 A | 5/1998 | Mazer et al. | |
| 5,779,668 A * | 7/1998 | Grabenkort | A61M 5/3129 |
| | | | 604/191 |
| 5,843,042 A | 12/1998 | Ren | |
| 6,029,946 A | 2/2000 | Doyle | |
| 6,036,669 A | 3/2000 | Cole et al. | |
| 6,277,092 B1 | 8/2001 | Cole et al. | |
| 6,290,206 B1 | 9/2001 | Doyle | |
| 6,482,170 B1 | 11/2002 | Andersen | |
| 6,541,802 B2 | 4/2003 | Doyle | |
| 6,752,790 B2 * | 6/2004 | Coombs | A61M 5/14 |
| | | | 604/251 |
| 6,962,563 B2 | 11/2005 | Yasunaga | |
| 7,560,686 B2 | 7/2009 | Bisch et al. | |
| 7,842,217 B2 | 11/2010 | Enns et al. | |
| 7,846,131 B2 | 12/2010 | Hudson et al. | |
| 7,921,847 B2 | 4/2011 | Totz | |
| 8,053,721 B2 | 11/2011 | Bisch et al. | |
| 8,162,916 B2 | 4/2012 | Knight | |
| 8,231,597 B2 | 7/2012 | Knight | |
| 8,366,697 B2 | 2/2013 | Knight | |
| 2004/0054350 A1 | 3/2004 | Shaughnessy et al. | |
| 2007/0060898 A1 | 3/2007 | Shaughnessy et al. | |
| 2008/0097348 A1 | 4/2008 | Itrich | |
| 2008/0171994 A1 * | 7/2008 | Williams | A61M 5/3135 |
| | | | 604/187 |
| 2008/0183153 A1 | 7/2008 | Enns | |
| 2011/0046568 A1 | 2/2011 | Enns et al. | |
| 2011/0270227 A1 | 11/2011 | Kleckner et al. | |
| 2012/0071853 A1 * | 3/2012 | Ingram | A61M 5/1452 |
| | | | 604/500 |
| 2012/0150111 A1 | 6/2012 | Hershey et al. | |
| 2012/0150112 A1 | 6/2012 | Hershey et al. | |
| 2012/0289936 A1 | 11/2012 | Ingram et al. | |

FOREIGN PATENT DOCUMENTS

| | | |
|---|---|---|
| EP | 0481250 A1 | 9/1991 |
| EP | 1110568 A2 | 6/2001 |
| EP | 1980282 A1 | 10/2008 |
| FR | 1126718 | 6/1955 |
| WO | 2007095541 A2 | 8/2007 |
| WO | 2009141510 A1 | 11/2009 |
| WO | 2011026156 A1 | 3/2011 |
| WO | 2012037082 A1 | 3/2012 |

OTHER PUBLICATIONS

International Search Report & Written Opinion for PCT/US13/53631; dated Oct. 11, 2013; 10 pgs.

* cited by examiner

SYSTEM AND METHOD FOR METERED ENTERAL FEEDING

CROSS-REFERENCE TO RELATED APPLICATION

This application claims the benefit of U.S. Provisional Patent Application Ser. No. 61/680,124 filed Aug. 6, 2012, the entirety of which is hereby incorporated herein by reference for all purposes.

TECHNICAL FIELD

The present invention relates generally to the field of enteral nutrition, and more particularly to an improved system and method for metering the delivery of nutrients to a human or animal subject, for example a neonatal infant, during enteral feeding.

BACKGROUND

Enteral feeding systems are generally utilized to supply nutrition to the human gastrointestinal tract through an enteral feeding tube. For example, in the field of enteral feeding systems, optional delivery methods can include an enteral pump, syringe pump, or gravity feed system. In some cases, it is desirable that the nutrients be metered to ensure the rate of delivery is appropriate.

Figure 1:
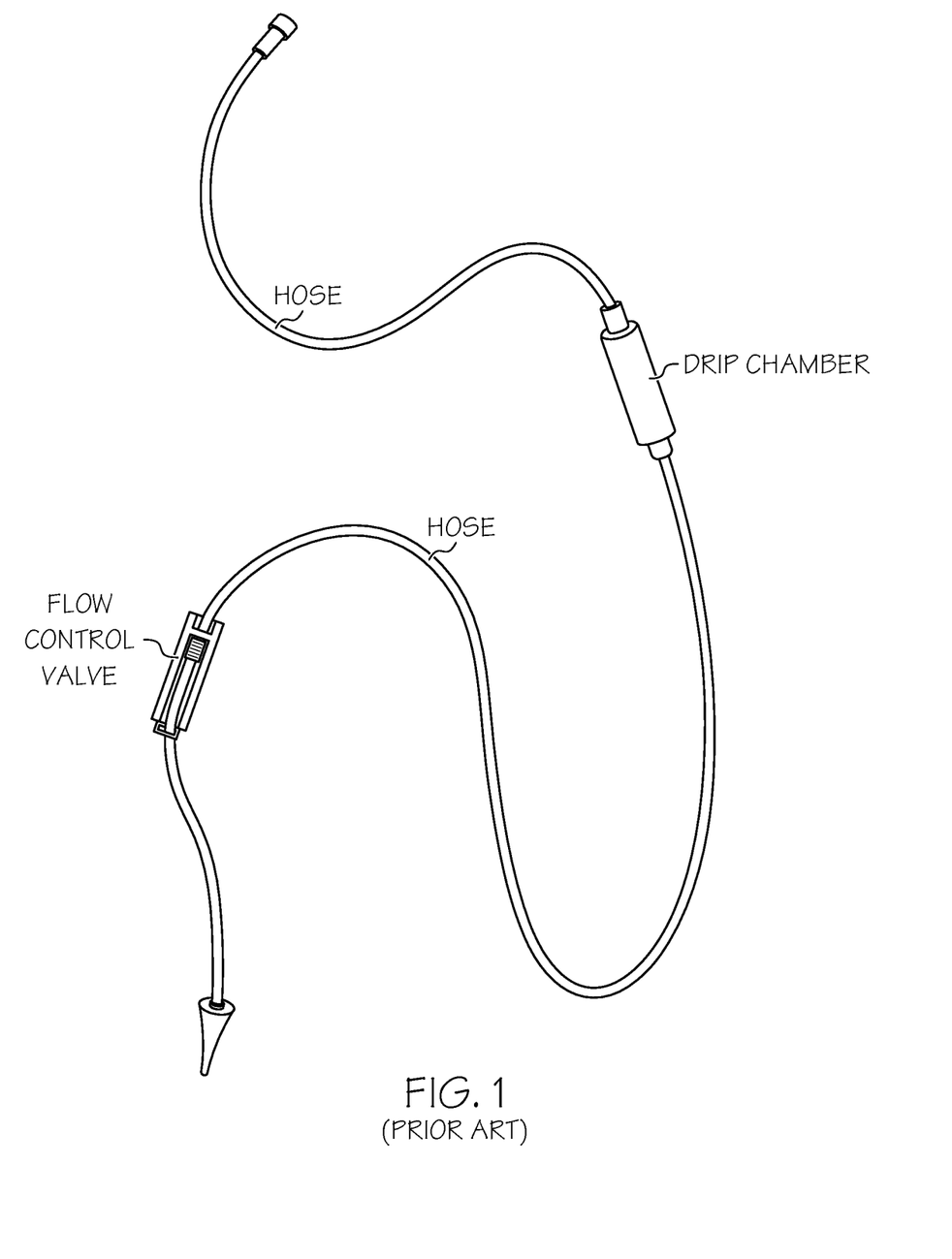
FIG. 1 is a perspective view of a primary portion of a metered enteral feeding system of known form.
Figure 2:
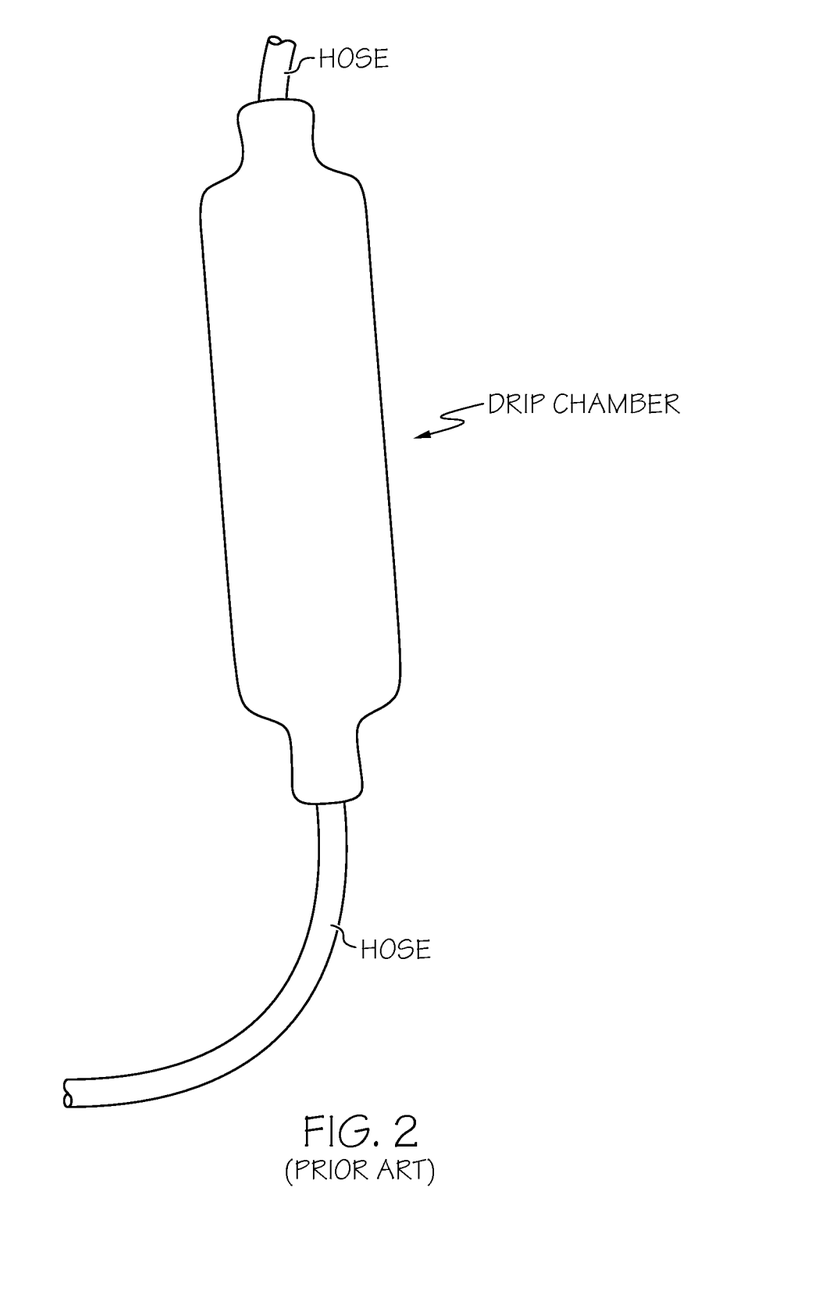
FIG. 2 is a perspective view of a drip chamber of FIG. 1.

The gravity feed system generally comprises a container, a hose connected between the container and the enteral feeding tube, a flow control valve to reduce or increase the opening of the tube carrying the nutrients therethrough, and a drip chamber to provide a monitor for calculating the rate of flow of the nutrients. An example of a portion of a metered enteral feeding system is shown in FIG. 1, which depicts two tubes coupled to either end of a drip chamber (see FIG. 2), wherein one of the tubes further includes a flow control valve. One drawback to known metered enteral feeding systems is the requirement to time a given number of drips of nutrients within the drip chamber to determine an approximate rate of flow, wherein a visual of the drip chamber is necessary to ensure a proper drip count, potentially leading to an incorrect rate of flow. Accordingly, improved metered enteral feeding systems are desirable.

It is to the provision of improved systems and methods for metered enteral feeding that the present invention is primarily directed.

SUMMARY

In example embodiments, the present invention provides improved systems and methods for metered enteral feeding. In one aspect, the present invention relates to a metered enteral feeding system having a vented syringe and a flow control valve. Optionally, the metered enteral feeding system further includes a length of tubing or hose. In example embodiments, the flow control valve adjustably secures to the tubing to control the rate of flow of a fluid flowing therethrough. Optionally, a first end of the tubing can communicate with the outlet of the syringe, and a second end of the tubing can communicate with an enteral feeding tube.

In one aspect, the invention relates to a metered enteral feeding system for delivering fluids. The metered enteral feeding system includes a vented syringe with a barrel defining a contained volume, a discharge port for discharging fluid contents from the contained volume, and a plunger repositionably mounted within the barrel between a venting position and a non-venting position. The barrel includes at least one vent for allowing airflow into the contained volume through the vent when the plunger is in the venting position and for preventing airflow into the contained volume through the vent when the plunger is in the non-venting position. The metered enteral feeding system also includes a flow control valve in fluid communication with the discharge port of the syringe. The fluid control valve is adjustable to provide an increased or decreased flowrate therethrough.

In another aspect, the invention relates to a method of metered enteral feeding of a fluid. The method includes delivering the fluid from a vented syringe to an enteral feeding tube and selectively operating a flow control valve to increase or decrease the rate of flow of the fluid flowing from the vented syringe to the enteral feeding tube.

In still another aspect, the invention relates to a method for metered enteral feeding. The method includes delivering a fluid from a vented syringe to an enteral feeding tube, and selectively operating a flow control valve to increase or decrease the rate of flow of the fluid flowing from the vented syringe to the enteral feeding tube. In example forms, the method may include delivery of the fluid from the vented syringe to the enteral feeding tube through a length of tubing or hose. Optionally, the method may additionally include monitoring the rate of flow of the fluid flowing from the vented syringe. The method may optionally also include determining a delivery rate by measuring a time interval during which a measured volume of fluid discharges from the vented syringe.

In still another aspect, the invention relates to a metered enteral feeding system for delivering fluids, the metered enteral feeding system including a vented container with contained volume for containing the fluids. The metered enteral feeding system includes a discharge port for discharging the fluid from the contained volume and at least one vent for allowing airflow into the contained volume. The metered enteral feeding system also includes a flow control valve in fluid communication with the discharge port of the vented container. The fluid control valve is adjustable to provide an increased or decreased flowrate therethrough.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 3:
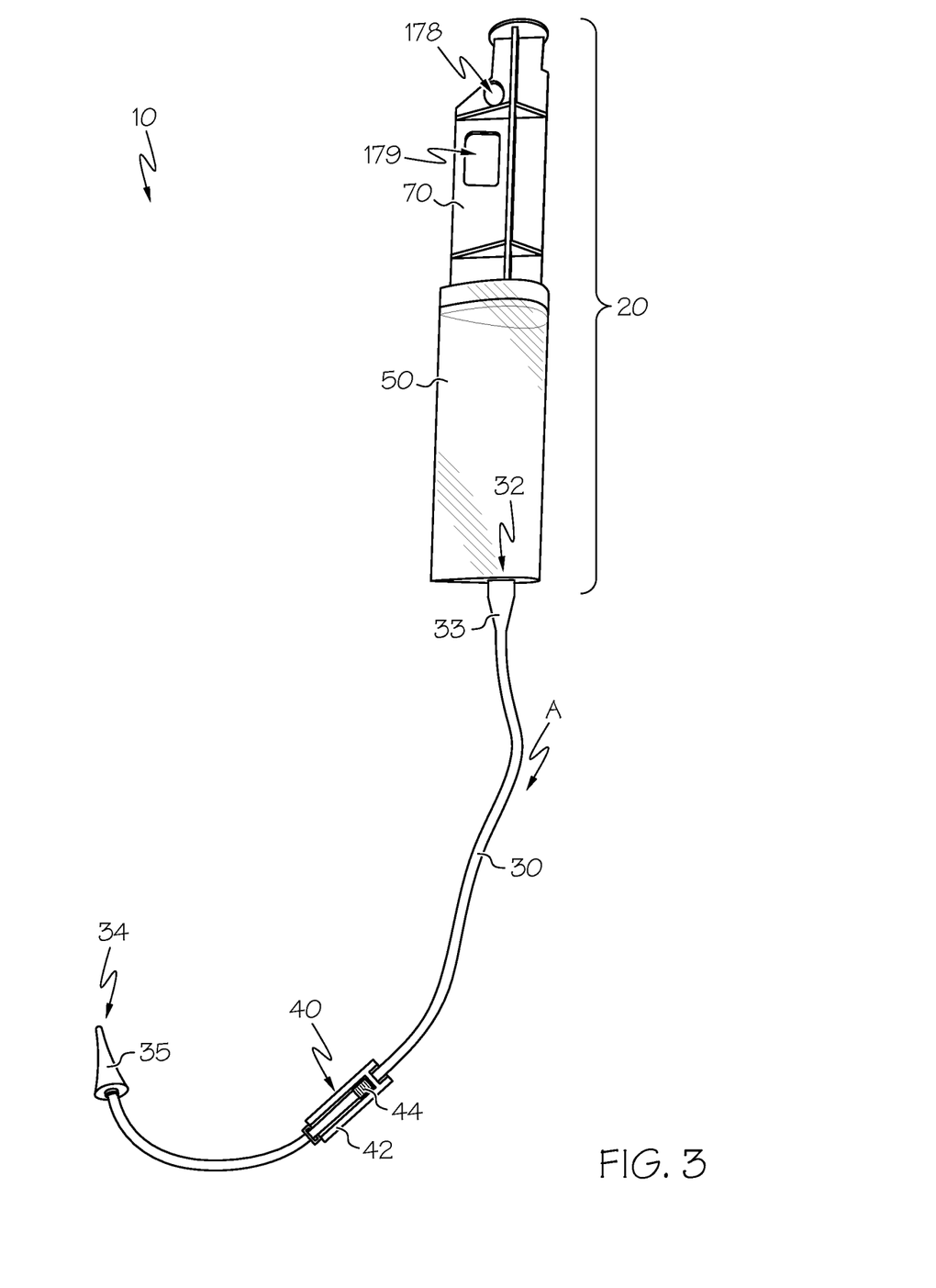
FIG. 3 is a perspective view of a metered enteral feeding system according to an example embodiment of the present invention.

With reference now to the drawing figures, wherein like reference numbers represent corresponding parts throughout the several views, FIG. 3 depicts an improved metered enteral feeding system 10 according to an example form of the present invention. In general, the metered enteral feeding system 10 includes a vented syringe 20, including a syringe 50 and a plunger 70, a length of tubing or hose 30 in fluid communication with the vented syringe 20, and an example flow control valve 40 coupled to the hose 30.

In example forms, the vented syringe 20 contains fluid nutrients to be supplied to the patient such that gravity discharges the nutrients from the vented syringe 20 and through the hose 30, wherein the flow control valve 40 coupled thereto provides for selective adjustment to the rate of flow of nutrients further flowing into the patient (A indicates the flow direction of nutrients). Preferably, the vented syringe 20 comprises viewable measurements or indicia that correspond to a measureable volume of nutrients therein, for example, showing the volume capacity or content level in cubic centimeters (cc) or milliliters (mL). As such, to calculate the rate of flow or flow rate of a fluid flowing from the syringe and through the hose to the enteral feeding tube where it is connected to the subject or patient, a time interval is taken for a given volume of nutrients removed therefrom, or alternatively a volume of fluid discharge is measured over a specified time period, with the delivery rate being determined by the delivery volume divided by time ($\Delta V/\Delta T$). Thus, depending on the calculated flow rate, the flow control valve 40 can be adjusted to result in a desired rate of flow.

Figure 4:
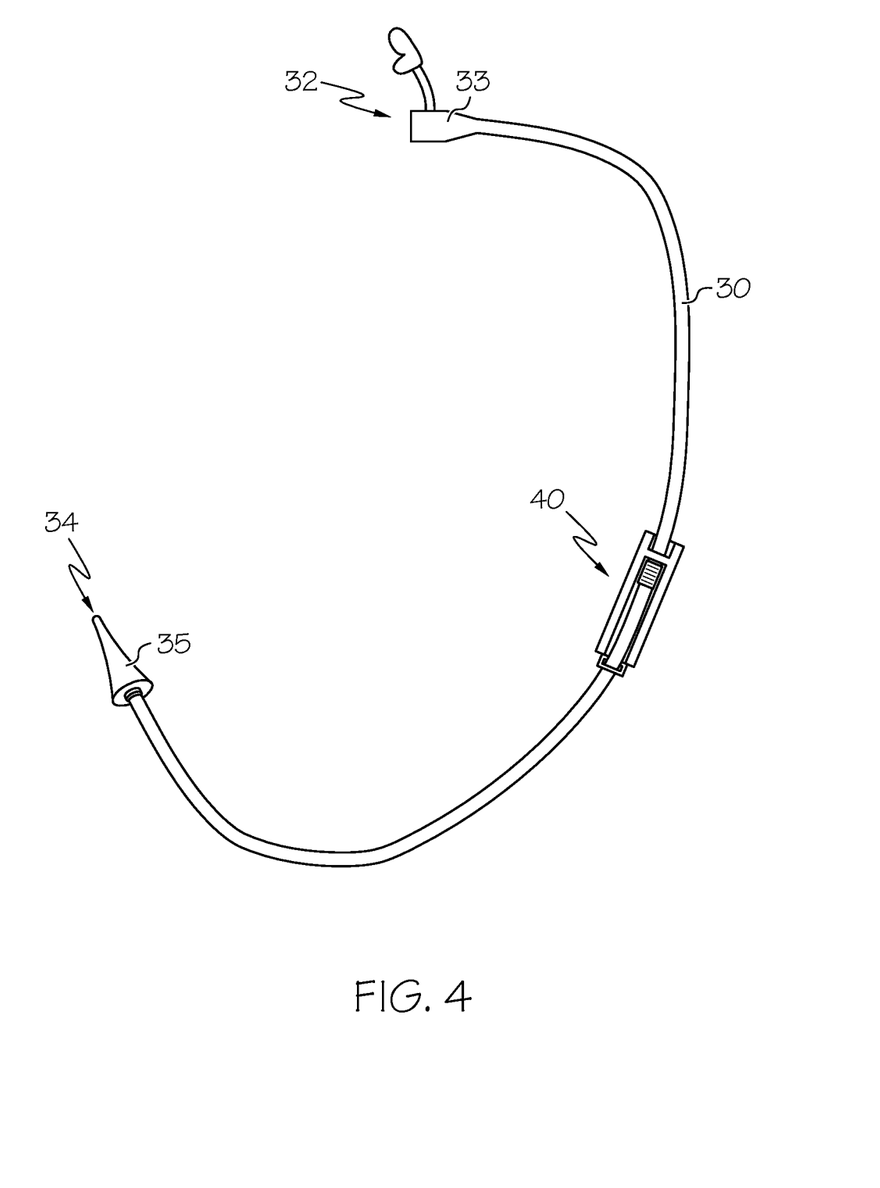
FIG. 4 shows a perspective view of a portion of the metered enteral feeding system of FIG. 3, showing a hose and an example flow control valve.
Figure 6A:
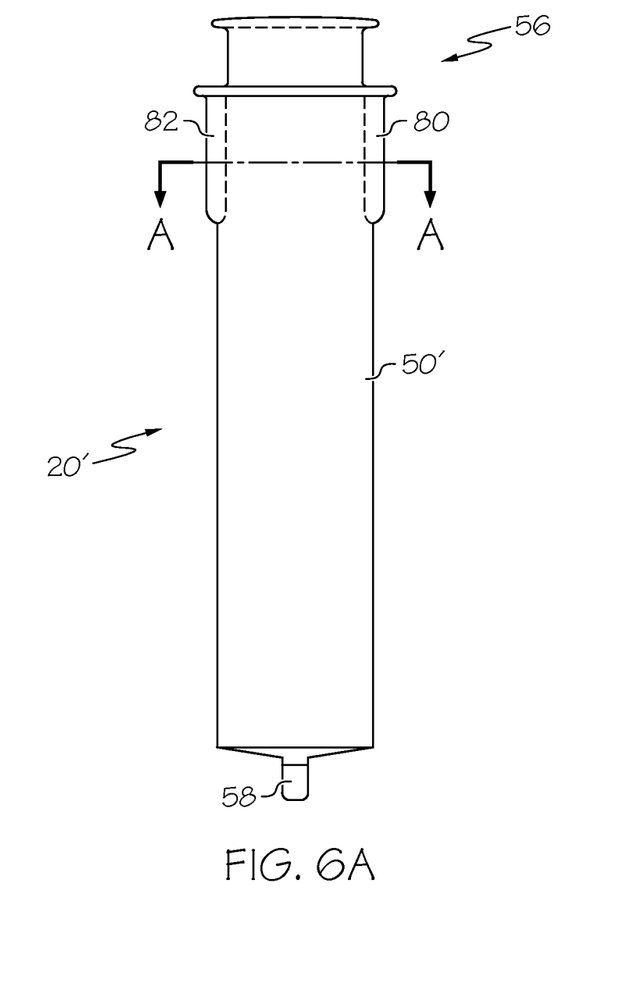
FIGS. 6A-6F show an example form of a vented syringe suited for use in connection with the system and method of the present invention.
Figure 6B:
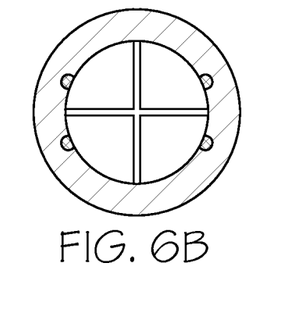
Figure 6C:
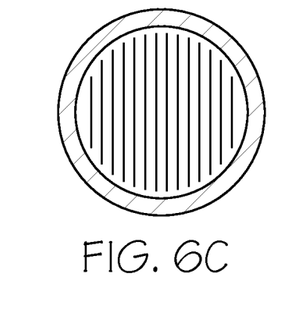
Figure 6D:
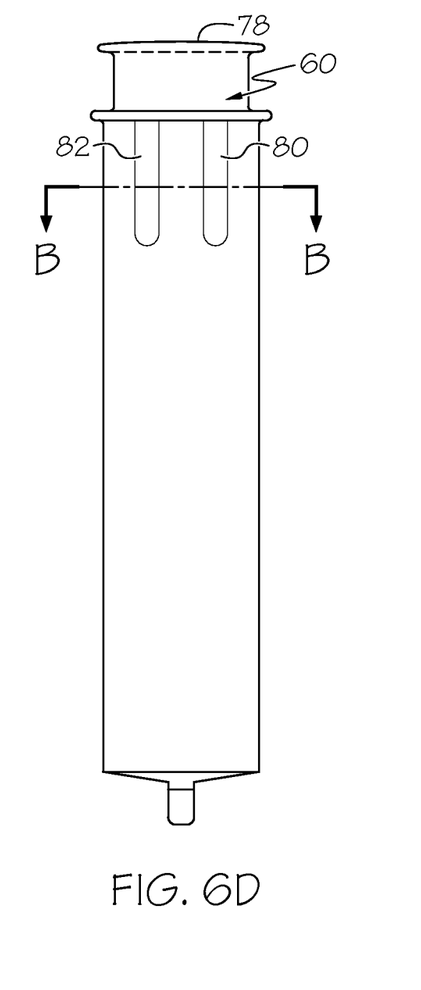
Figure 6E:
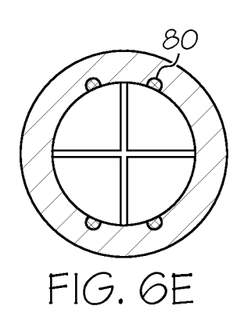
Figure 6F:
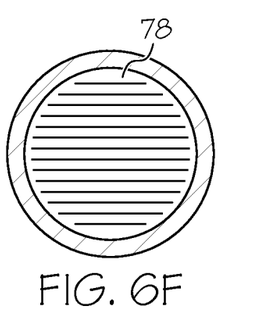
Figure 9A:
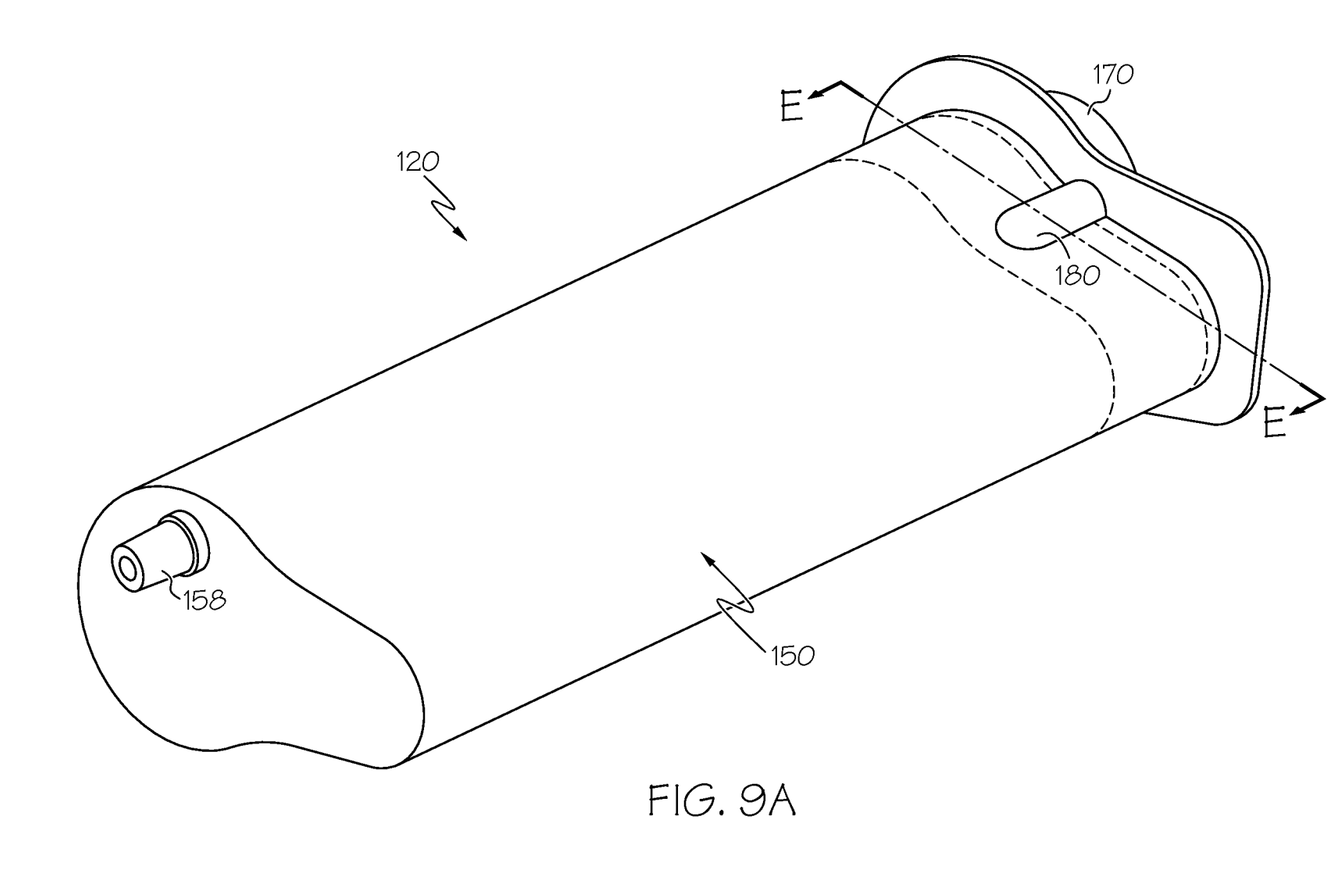
FIG. 9A is a perspective view of another vented syringe suited for use in connection with the system and method of the present invention according to an example form.
Figure 9B:
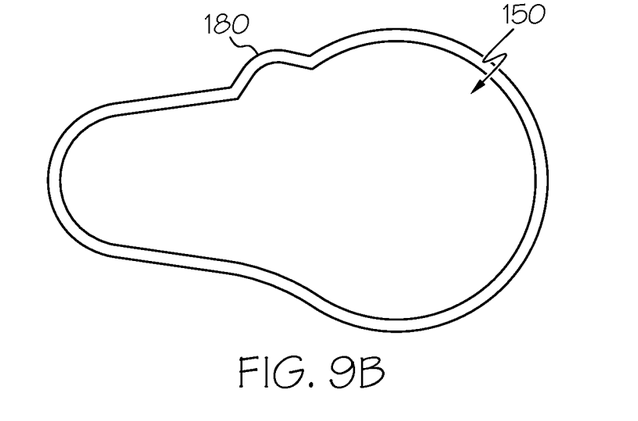
FIG. 9B is a longitudinal cross-section view of the enteral syringe of FIG. 9A take at line E-E.
Figure 9C:
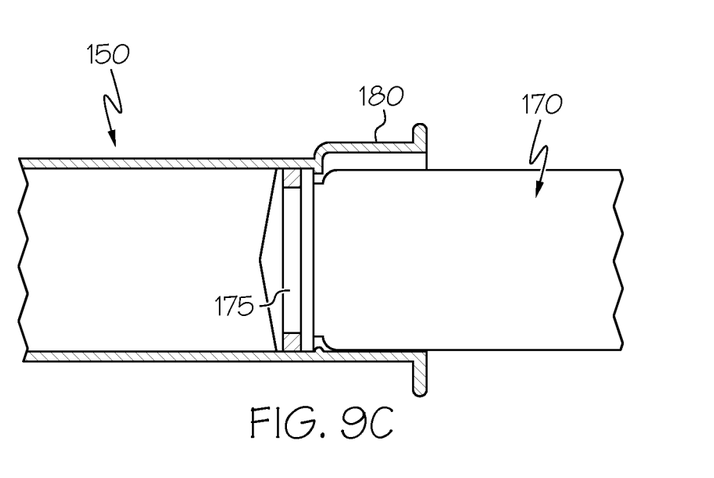
FIG. 9C is an isolated cross-sectional side view of the enteral syringe of FIG. 9A, shown with the plunger in a first or closed position.
Figure 9D:
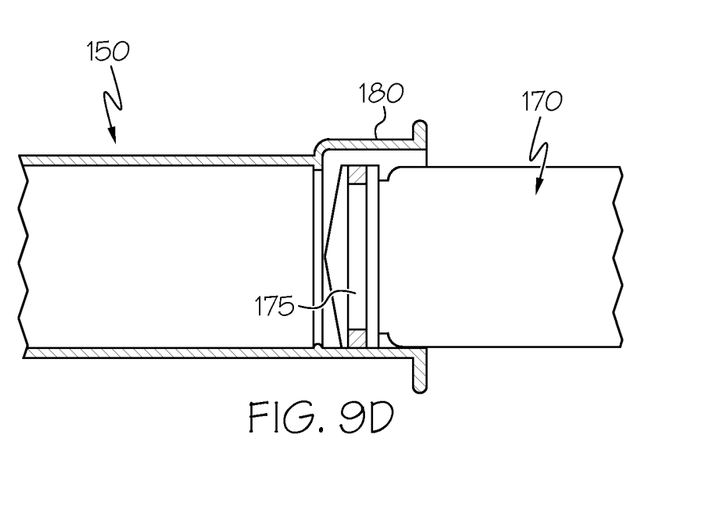
FIG. 9D is an isolated cross-sectional side view of the enteral syringe of FIG. 9A, shown with the plunger in a second or vented position.

FIG. 4 shows the hose 30 with a proximal end 32 having an intake female connector 33 and a distal end 34 having a dispense male connector 35. The hose 30 is preferably constructed of flexible material, for example plastic or rubber. The intake connector 33 is preferably sized and shaped to provide removable engagement with a nipple or tip (unshown) (see 58, 158 in FIGS. 6A and 9A) of the vented syringe 20, and the dispense connector 35 is preferably sized and shaped to provide engagement with the enteral feeding tube (unshown).

Figure 5:
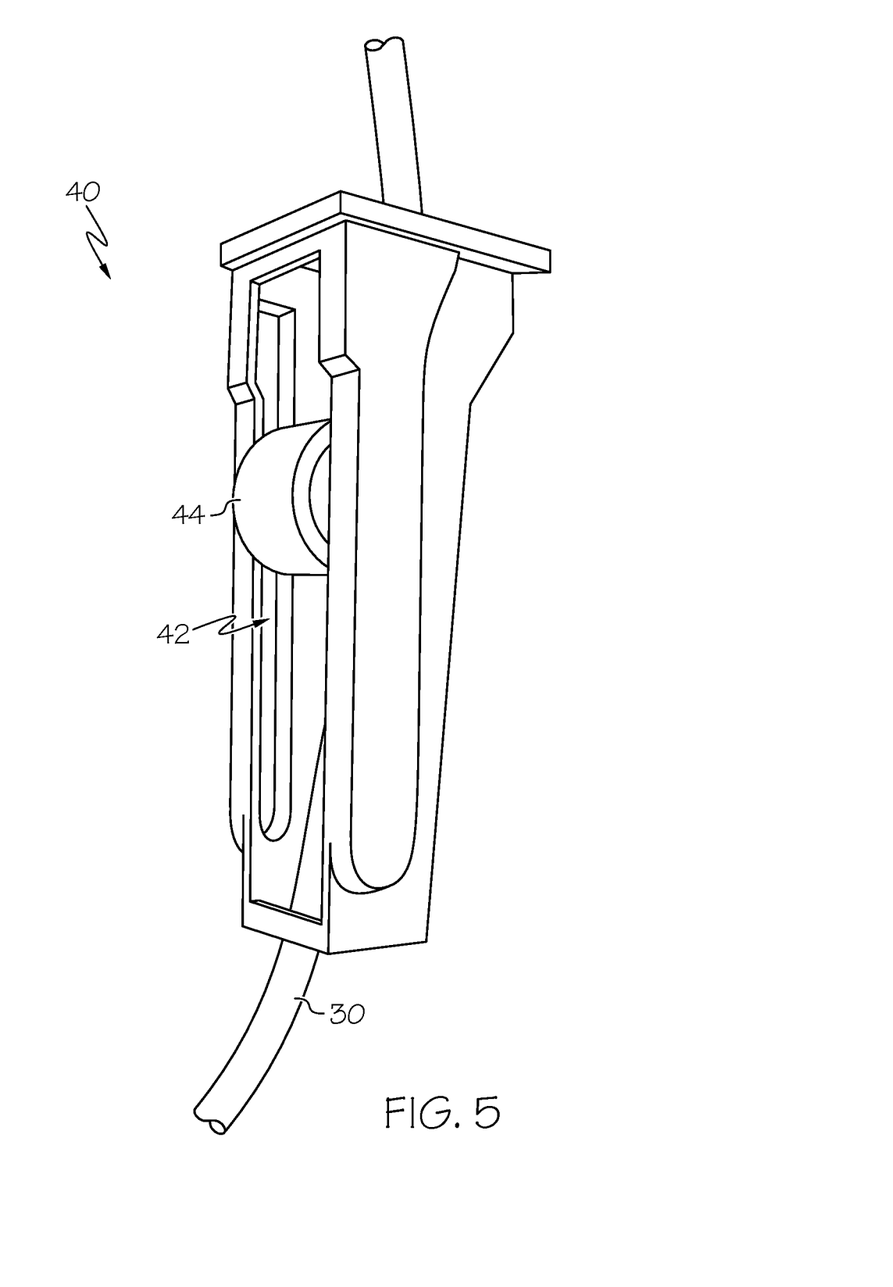
FIG. 5 shows a perspective view of the example flow control valve of FIG. 4.

As depicted in FIGS. 3, 4 and 5, the example flow control valve 40 couples to the hose 30 between the proximal and distal ends 32, 34 and can selectively reduce or increase the rate of flow of the nutrients or a fluid flowing therethrough. As depicted, the example flow control valve 40 can have a hollow interior with an open side. The depicted flow control valve 40 has a ramped surface opposite the open side. The inner side and the outer side of the ramped surface extend in parallel, so the ramped surface has a consistent thickness. As depicted, the ramped surface is angled inward from a first end to a second end of the flow control valve. As depicted, the flow control valve 40 can have a pair or oppositely positioned sidewalls extending between the ramped surface and the open side. As depicted, a pair of oppositely positioned elongate channels 42 (one of the pair is unshown) extend along an interior surface of each sidewall. The ramped surface is angled with respect to the pair of elongate channels 42, so that the distance between the elongate channel and the ramped surface is variable depending on the position along the flow control valve 40. The inner side of the ramped surface can have at least one ridge or grip feature (unshown) located substantially toward the end with a shorter distance between the elongate channel 42 and the ramped surface.

As depicted, the hose 30 extends through the hollow interior of the flow control valve. The example flow control valve 40 can have open ends, for example apertures, (unshown) located on each end to enable the passage of the hose 30 therethrough.

In an example form, the rate of flow is determined by the position of an eccentrically mounted and adjustable compressor roller or wheel 44 along the elongate guide channels 42. The compressor roller or wheel 44 is movably mounted along the elongated guide channels 42, for example through a pair of opposing axles (unshown) that extend within the guide channels. For example, the longitudinal position of the compressor wheel 44 relative to an end of the guide channels 42 alters the transverse distance between the compressor wheel 44 and an internal surface of the guide channels such that the hose 30 is incrementally compressed by the compressor wheel towards the inner side of the ramped surface, causing reduction to the opening within the hose 30, thus a reduction to the rate of flow of the nutrients flowing therethrough. Rolling the compressor wheel 44 in the opposing direction along the pair of guide channels 42 releases the compressive force on the hose 30, thus increasing the rate of flow. The compressor roller or wheel 44 can be temporarily fixed in a position on the hose 30, for example in compressive alignment with the at least one of the ridge or grip features (unshown) on the ramped surface. Preferably, the vented syringe 20 provides at least one vent to allow gravity discharge of fluid from the nozzle of the syringe.

Figure 7A:
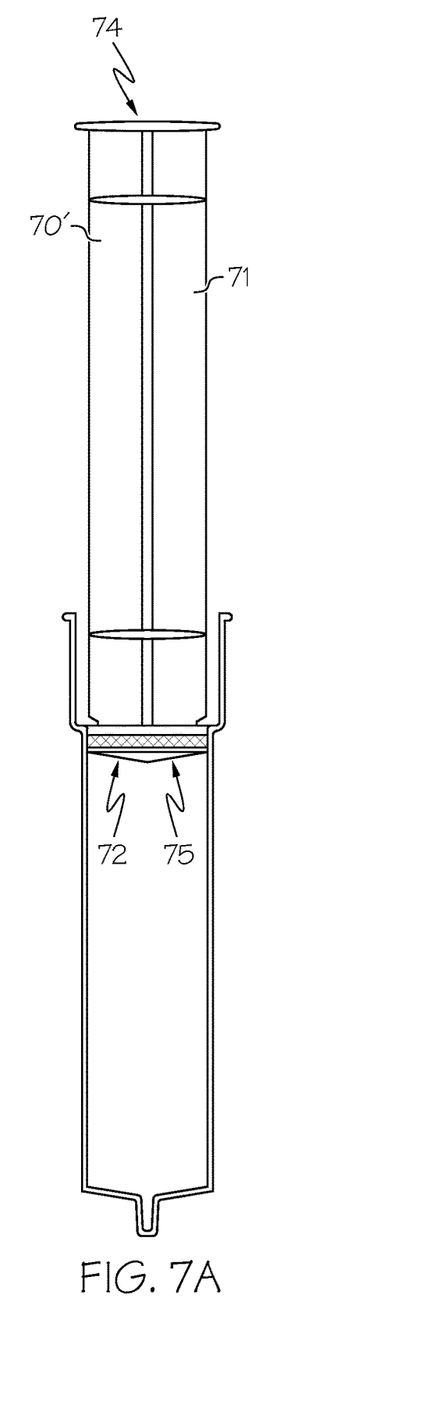
FIGS. 7A-7B show cross-sectional views of the vented syringe of FIG. 6.
Figure 7B:
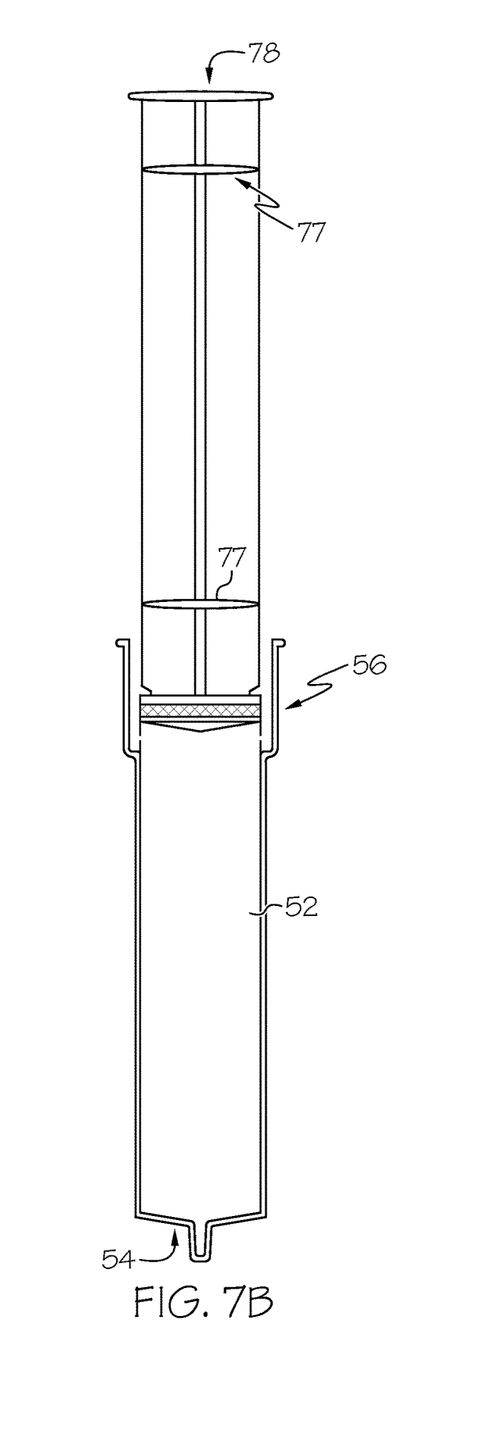
Figure 8A:
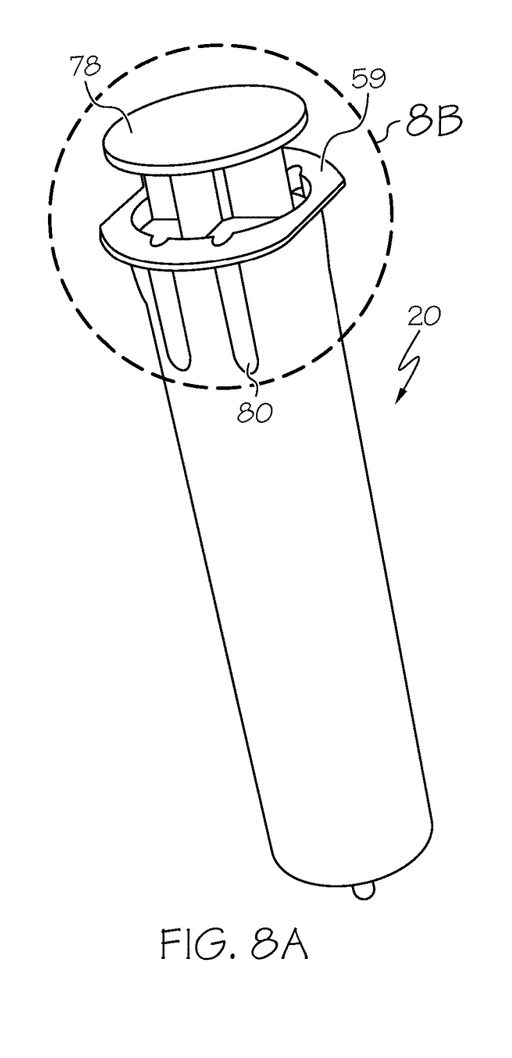
FIGS. 8A-8B show perspective views of the vented syringe of FIG. 6.
Figure 8B:
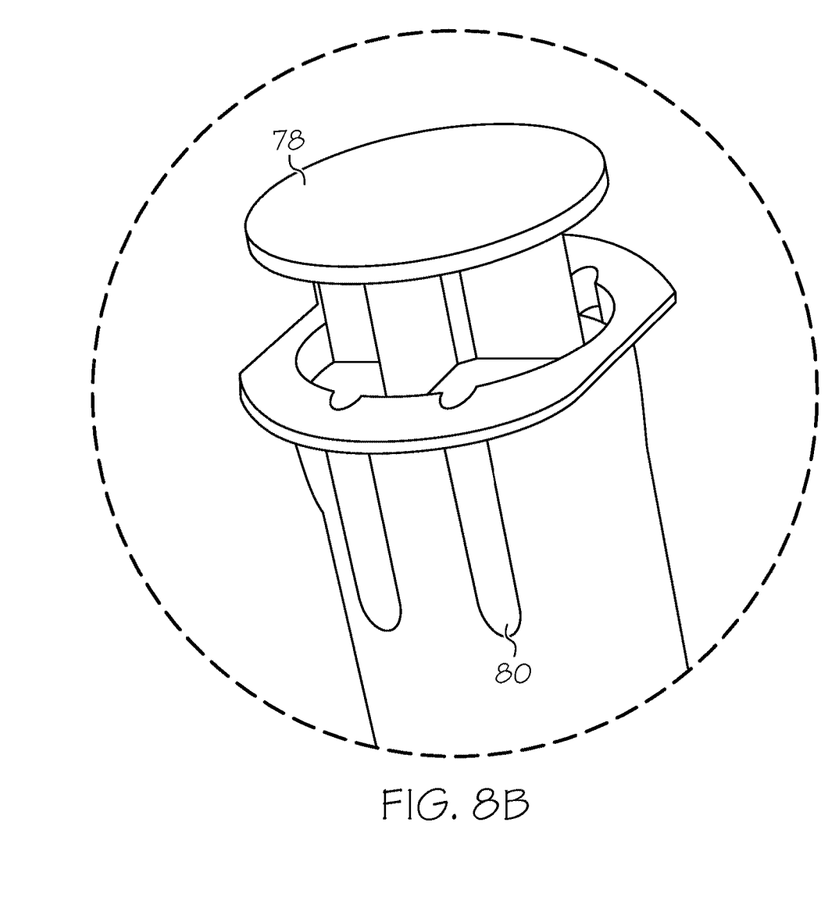

FIGS. 6-8 show another example vented syringe 20' that can be used with the previously described metered enteral feeding system 10. U.S. patent application Ser. No. 13/231, 185 and U.S. Provisional Patent Application Ser. No. 61/418,963 are incorporated herein for further details of example forms of syringe construction adaptable for use in connection with the system and method of the present invention. The vented syringe 20' includes an elongated syringe body 50' and a plunger 70'. The syringe body 50' defines an internal elongate cavity 52 that extends substantially along the length of the body from a proximal end 56 towards distal end 54. The distal end 54 of the syringe body 50' comprises a nozzle or tip 58 with a discharge lumen in fluid communication with the internal elongate cavity 52. The tip 58 of the syringe body 50' is preferably adapted for connection to the proximal end 32 of the hose 30 (as depicted in FIG. 3). The proximal end 56 of the syringe body 50' includes an opening 60 for receiving the plunger 70' therein. In an example embodiment, the syringe is a 100 mL syringe. In another example embodiment, the syringe volume can vary, for example from a 5 mL syringe to a 500 mL syringe. The syringe body 50' can have a substantially circular cross-section or can comprise a non-circular, oval, elliptical, rectangular, or asymmetric cross-section as desired (see FIGS. 9A-9D).

The plunger 70' includes an elongated body 71 sized to be inserted into the opening 60 of the syringe body 50', the body or arm having a distal end 72 and a proximal end 74. The distal end 72 comprises a sealing head 75 for tightly engaging an inner wall of the body cavity 52. The sealing head and/or gasket 75 substantially mirrors the cross-section and diameter of the cavity 52 to provide an appropriate seal between the head and the cavity. In example embodiments, the sealing head 75 frictionally engages the inner wall of the cavity 52 such that the plunger 70' remains in a particular position within the syringe body 50' absent user manipulation. The plunger body 71 also comprises at least one, and preferably two or more ribs 77 that extend to fit within the cross-section and/or diameter of the cavity 52. Thus, as the plunger 70' is selectively inserted into the cavity 52 of the syringe body 50' and travels therein during use, the ribs 77 operate to keep the plunger 70' aligned within the cavity 52 and prevent the plunger from tipping within the same. As such, the ribs 77 help maintain an adequate seal between the plunger head 75 and the wall of the cavity 52. The proximal end 74 the plunger 70 includes a contact face 78 to permit user manipulation.

In order to permit the syringe 20' to be vented during use (without fully removing the plunger 70' from the syringe body 50', the syringe body includes one or more vents 80. The vents 80 permit the passage of air into the syringe body cavity 52 when in use to prevent the buildup of a vacuum within the syringe. In the depicted example embodiments, each vent 80 comprises a channel 82 that extends from the proximal end 56 of the syringe barrel along a portion of the barrel's length, into the inner cavity 52 of the syringe body 50'. While example depicted embodiments depict four vents 80, alternative embodiments can include one vent, two vents, three vents, or five or more vents as desired, as well as alternate vent configurations. The syringe plunger 70' is selectively positionable within the barrel in one or more closed/unvented positions where the contained volume within the syringe is sealed to prevent air passage in or out, or one or more open/vented positions wherein air can pass in and out of the syringe.

FIGS. 9A-9D depict another example vented syringe 120 suited for use in connection with the previously described metered enteral feeding system 10. The syringe 120, as depicted, has a non-circular non-symmetrical key-way cross-sectional syringe body 150 and a plunger 170 that has a gasket 175 at the distal end. The body 150 and the plunger 170 have similar elements and coordinate with each other in a similar manner to the embodiment described in FIGS. 6-8. The syringe also includes similar characteristics, for example a tip 158 and at least one vent 180, and additionally operates through mechanics similar to the embodiment described in FIGS. 6-8. The plunger 170 preferably comprises at least one opening or cut-out (depicted as a first cut-out 178 and a second cut-out 179 in FIG. 3) such that the vented syringe can be suspended during feeding, for example a hook from an IV stand can be inserted therethrough to accommodate hanging the syringe in a substantially vertical orientation or at an oblique angle relative to the vertical.

In operation, the metered enteral feeding system 10 can be used to deliver nutrients to a subject and provide for calculating the rate of flow of a fluid flowing therethrough in part by visualization of the nutrients or fluid contained within the syringe 50, 150. To begin the metered enteral feeding procedure, the flow control valve 40 is adjusted to prevent the fluid from flowing through the hose 30. The syringe is then filled with the nutrients and the plunger can be placed within the same such that the valve 80, 180 is closed, for example, wherein the sealing head 75, 175 frictionally engages the inner wall of the cavity 52. The distal end 34 of the hose 30 is then connected to the enteral feeding tube that is further connected to the subject.

When the delivery of nutrients is desired, the flow control valve 40 is adjusted to allow for the maximum flow of nutrients therethrough, and the plunger is placed in the vented position. As the rate of feeding is less critical than the rate of delivery of medication, the time interval is measured for the removal of a measureable volume of fluid or nutrients from the vented syringe 20, 20', 120 for example, a reduction in volume of about 5 milliliters. Once the time interval is taken, the flow rate can be calculated, for example, by dividing the reduction in volume of the fluid or nutrients therein by the elapsed time. For example, if it is determined that a time interval of about 15 seconds corresponds to a reduction in volume of about 5 mL, the 5 mL volume reduction is divided by the 15 second time interval to equal a flow rate or rate of flow of about 0.33 mL/s. Thus, depending on the calculated flow rate, the flow control valve 40 is adjusted to increase or decrease the rate of flow until a specified flowrate is achieved. Alternatively, the number and/or size of the vents can be varied to affect the rate of flow with or without use of the flow control valve.

In example embodiments, the metered enteral food delivery system 10 comprises one or more food-grade plastics (i.e. polypropylene), other polymers, glass, metals, metal alloys, resins, rubbers, rubber derivatives, elastomerics (i.e. santoprene), silicones or other materials of construction. Optionally, colorants and/or other additives may be included. As described above, the syringe can include external markings or other indicia, for example to indicate volume capacity and/or content levels. In further embodiments, a standard syringe with its plunger removed, or an open or vented container with an exit port can be used in place of the vented syringe.

While the invention has been described with reference to preferred and example embodiments, it will be understood by those skilled in the art that a variety of modifications, additions and deletions are within the scope of the invention, as defined by the following claims.

What is claimed is:

1. A metered enteral feeding system for delivering fluids, the metered enteral feeding system comprising:
   a vented syringe comprising a barrel defining a contained volume, a discharge port for discharging fluid contents from the contained volume, and a plunger configured to be repositionably mounted within the barrel between a venting position and a non-venting position without removing the plunger from the barrel, the barrel comprises at least one vent protruding from a portion of an exterior surface of the barrel for allowing airflow into the contained volume through the vent when the plunger is in the venting position and for preventing airflow into the contained volume through the vent when the plunger is in the non-venting position, wherein the plunger is configured to be mounted within the barrel in the venting position when the discharge port is discharging fluid contents; and
   a flow control valve in fluid communication with the discharge port of the syringe, the fluid control valve being adjustable to provide an increased or decreased flowrate therethrough.

2. The metered enteral feeding system of claim 1, further comprising a length of tubing providing fluid communication between the discharge port of the syringe and the flow control valve.

3. The metered enteral feeding system of claim 2, wherein the flow control valve adjustably secures to the tubing to control the rate of flow of a fluid flowing therethrough.

4. The metered enteral feeding system of claim 2, wherein the flow control valve is configured to apply a releasable compressive force to the tubing to control the rate of flow of fluid flowing therethrough.

5. The metered enteral feeding system of claim 2, wherein a first end of the tubing communicates with an outlet of the vented syringe.

6. The metered enteral feeding system of claim 2, wherein a second end of the tubing communicates with an enteral feeding tube.

7. The metered enteral feeding system of claim 1, wherein the flow control valve comprises at least one elongated channel and an adjustable roller movably secured within the at least one elongated channel.

8. The metered enteral feeding system of claim 7, wherein the flow control valve further comprises a ramp surface extending at an oblique angle with respect to the at least one elongated channel.

9. The metered enteral feeding system of claim 1, wherein the plunger comprises at least one cut-out configured to receive a hanging hook.

10. The metered enteral feeding system of claim 1, wherein the fluids are discharged from the vented syringe through gravity.

11. A metered enteral feeding system for delivering fluids, the metered enteral feeding system comprising:
    a vented container comprising contained volume for containing the fluids, a discharge port for discharging the fluid from the contained volume, and at least one vent protruding from a portion of an exterior surface of the container for allowing airflow into the contained volume, wherein a plunger repositionably mounts within the container without being removed from the container such that at least one position of the plunger prevents airflow into the contained volume and at least one position of the plunger allows airflow into the contained volume, wherein the plunger is configured to be mounted within the container in the at least one position allowing airflow into the contained volume when the discharge port is discharging fluid from the contained volume; and
    a flow control valve in fluid communication with the discharge port of the vented container, the fluid control valve being adjustable to provide an increased or decreased flowrate therethrough.

12. The metered enteral feeding system of claim 11, wherein the vented container comprises a syringe barrel.

13. The metered enteral feeding system of claim 11, wherein the vented container is configured to discharge the fluid through the discharge port through gravity.

14. The metered enteral feeding system of claim 11, further comprising a flexible tube delivering the fluids from the discharge port, the flow control valve configured to adjust the flowrate of the fluids within the flexible tube.

15. The metered enteral feeding system of claim 14, wherein the flow control valve applies adjustable compressive force to the flexible tube to adjust the flowrate of the fluids within the flexible tube.

* * * * *